US009328047B2

(12) United States Patent
Miller et al.

(10) Patent No.: US 9,328,047 B2
(45) Date of Patent: May 3, 2016

(54) PROCESS FOR STABILIZING A PHOSPHITE LIGAND AGAINST DEGRADATION

(71) Applicant: Dow Technology Investments LLC, Midland, MI (US)

(72) Inventors: Glenn A. Miller, South Charleston, WV (US); Thomas C. Eisenschmid, Cross Lanes, WV (US); Michael A. Brammer, Lake Jackson, TX (US); Rick B. Watson, Missouri City, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/429,672

(22) PCT Filed: Sep. 9, 2013

(86) PCT No.: PCT/US2013/058714
§ 371 (c)(1),
(2) Date: Mar. 19, 2015

(87) PCT Pub. No.: WO2014/051975
PCT Pub. Date: Apr. 3, 2014

(65) Prior Publication Data
US 2015/0232403 A1 Aug. 20, 2015

Related U.S. Application Data

(60) Provisional application No. 61/705,194, filed on Sep. 25, 2012.

(51) Int. Cl.
*C07F 9/30* (2006.01)
*C07C 45/50* (2006.01)

(52) U.S. Cl.
CPC .................... *C07C 45/505* (2013.01)

(58) Field of Classification Search
USPC ................................. 568/8, 13, 454
See application file for complete search history.

(56) References Cited

U.S. PATENT DOCUMENTS

| | | | |
|---|---|---|---|
| 3,527,809 A | 9/1970 | Pruett et al. | |
| 4,148,830 A | 4/1979 | Pruett et al. | |
| 4,247,486 A | 1/1981 | Brewester et al. | |
| 4,329,507 A | 5/1982 | Takeda et al. | |
| 4,518,809 A | 5/1985 | Forster et al. | |
| 4,528,403 A | 7/1985 | Tano et al. | |
| 4,567,306 A | 1/1986 | Dennis et al. | |
| 4,593,127 A | 6/1986 | Bunning et al. | |
| 4,599,206 A | 7/1986 | Billig et al. | |
| 4,668,651 A | 5/1987 | Billig et al. | |
| 4,717,775 A | 1/1988 | Billig et al. | |
| 4,748,261 A | 5/1988 | Billig et al. | |
| 4,769,498 A | 9/1988 | Billig et al. | |
| 4,774,361 A | 9/1988 | Maher et al. | |
| 4,835,299 A | 5/1989 | Maher et al. | |
| 4,885,401 A | 12/1989 | Billig et al. | |
| 5,102,505 A | 4/1992 | Sorensen | |
| 5,110,990 A | 5/1992 | Blessing et al. | |
| 5,113,022 A | 5/1992 | Abatjoglou et al. | |
| 5,179,055 A | 1/1993 | Wink et al. | |
| 5,202,297 A | 4/1993 | Lorz et al. | |
| 5,235,113 A | 8/1993 | Sato et al. | |
| 5,254,741 A | 10/1993 | Lorz et al. | |
| 5,264,616 A | 11/1993 | Roeper et al. | |
| 5,288,918 A | 2/1994 | Maher et al. | |
| 5,312,996 A | 5/1994 | Packett | |
| 5,360,938 A | 11/1994 | Babin et al. | |
| 5,364,950 A * | 11/1994 | Babin et al. | 556/2 |
| 5,391,801 A | 2/1995 | Sato et al. | |
| 5,430,194 A | 7/1995 | Barner et al. | |
| 5,491,266 A | 2/1996 | Babin et al. | |
| 5,527,950 A | 6/1996 | Hansen et al. | |
| 5,681,473 A | 10/1997 | Miller et al. | |
| 5,710,344 A | 1/1998 | Breikss et al. | |
| 5,728,893 A | 3/1998 | Becker et al. | |
| 5,731,472 A | 3/1998 | Leung et al. | |
| 5,731,473 A | 3/1998 | Bryant et al. | |
| 5,741,942 A | 4/1998 | Bryant et al. | |
| 5,741,944 A | 4/1998 | Bryant et al. | |
| 5,744,649 A | 4/1998 | Bryant et al. | |
| 5,767,321 A | 6/1998 | Billig et al. | |
| 5,874,640 A * | 2/1999 | Bryant et al. | 568/454 |
| 5,929,289 A | 7/1999 | Abatjoglou et al. | |
| 6,265,620 B1 | 7/2001 | Urata et al. | |
| 6,440,891 B1 | 8/2002 | Maas et al. | |
| 6,693,219 B2 | 2/2004 | Puckette et al. | |
| 7,009,068 B2 | 3/2006 | Schmutzler et al. | |
| 7,145,042 B2 | 12/2006 | Volland et al. | |
| 7,196,230 B2 | 3/2007 | Peng et al. | |
| 7,586,010 B2 | 9/2009 | Liu et al. | |
| 7,615,645 B2 | 11/2009 | Volland et al. | |
| 7,674,937 B2 | 3/2010 | Tolleson et al. | |
| 7,872,156 B2 | 1/2011 | Liu et al. | |
| 8,003,816 B2 | 8/2011 | Selent et al. | |
| 2012/0172630 A1 | 7/2012 | Liu | |
| 2013/0261344 A1 | 10/2013 | Miller et al. | |
| 2014/0051568 A1 | 2/2014 | Eisenschmid et al. | |

FOREIGN PATENT DOCUMENTS

WO 8808835 11/1988

OTHER PUBLICATIONS

CRC Handbook of Chemistry and Physics, 72nd Ed., 1991-1992, CRC Press, p. 1-10.

(Continued)

*Primary Examiner* — Sudhakar Katakam
*Assistant Examiner* — Pancham Bakshi

(57) ABSTRACT

A process for stabilizing a phosphite ligand against degradation in a hydroformylation reaction fluid, said process comprising adding an epoxide to the reaction fluid, and further comprising separating one or more phosphorus acidic compounds from the reaction fluid by treating the reaction fluid with an aqueous buffer solution under conditions sufficient to neutralize and remove at least some amount of the phosphorus acidic compounds from the reaction fluid.

11 Claims, 1 Drawing Sheet

(56) References Cited

OTHER PUBLICATIONS

Guo, et al., Hydroformylation of 1-hexene with Pt(P(m-C6H4SO3Na)3)2Cl2 and its tin chloride analogue on a controlled-pore glass, Journal of Molecular Catalysis, 1991, 70, p. 363-368.
Toth, et al., "Immobilization of HRh(CO)(P(m-C6H4SO3Na)3)3 on an Anion Exchange Resin for the Hydroformylation of Higher Olefins", Catalysis Letters, 1991, 8, p. 209-214.
Guo, et al., "Bis[tris(m-(sodium sulfonato)phenyl)phosphine] hexacarbonyl dicobalt, Co2(CO)6(P(m-C6H4SO3Na)3)2, in a supported aqueous phase for the hydroformylation of 1-hexene" Journal of Organometallic Chememistry, 1991,403, p. 221-227.
Arhancet, et al., "Hydroformylation by supported aqueous-phase catalysis: a new class of heterogeneous catalysts" Nature, Jun. 8, 1989, 339, p. 454-455.
Rode, et al., "Propylene Hydroformylation on Rhodum Zeolites X and Y", Journal of Catalysis, 1985, 96, p. 563-573.
Davis, et al., "Hydroformylation of 1-hexene by soluble and zeolite-supported rhodium species Part II", Journal of Molecular Catalysis, 1987, 39, p. 243-259.
Feldman, et al., "Membrane-supported rhodium hydroformylation catalysts", Journal of Molecular Catalysis, 1990, 63, p. 213-221.
Jongsma, et al., "Fine tuning of bulky-phosphite modified rhodium catalysts by binding them to copolymers", Journal of Molecular Catalysis, 1993, 83, p. 17-35.
Lieto, et al., "Polymeric supports for catalysts", Chemtech, 13, No. 1, Jan. 1983, p. 46-53.
Parrinello, et al., "Asymmetric Hydroformylation Catalyzed by Homogeneous and Polymer-Supported Platinum Complexes Containing Chiral Phosphine Ligands", Jounal of American Chemical Society, 1987, 109, p. 7122-7127.
Jongsma, et al., "A new type of highly active polymer-bound rhodium hydroformylation catalyst", Polymer, 1992, 33, p. 161-165.
Bergbreiter, et al., "Polyethylene-Bound Soluble Recoverable Palladium(0) Catalysts", J. Org. Chem. 1989, 54, p. 2726-2730.
Mata-Perez, et al., "The Kinetic Rate Law for Autocatlytic Reactions", Journal of Chemical Education, vol. 64, No. 11, Nov. 1987, p. 925-927.
J. Mol. Cat. 1991, 70, 363-368.
Catal. Lett. 1991, 8, 209-214.
J. Organomet. Chem., 1991, 403, 221-227.
Nature 1989, 339, 454-455.
J. Catal. 1985, 96, 563-573.
J. Mol. Cat. 1987, 39, 243-259.
J. Mol. Cat. 1990, 63, 213-221.
J. Mol. Cat. 1993, 83, 17-35.
Chemtech 1983, 46.
J. Am. Chem. Soc. 1987, 109, 7122-7127.
Polymer 1992, 33, 161.
J. Org. Chem. 1989, 54, 2726-2730.
The Kinetic Rate Law for Autocatlytic Reactions, Mata-Perez et al, Journal of Chemical Education, vol. 64, No. 11 Nov. 1987, pag 925-927.
PCT/US2013/058714, Oct. 29, 2013, International Search Report and Written Opinion.
PCT/US2013/058714, Apr. 9, 2015, International Preliminary Report on Patentability.

\* cited by examiner

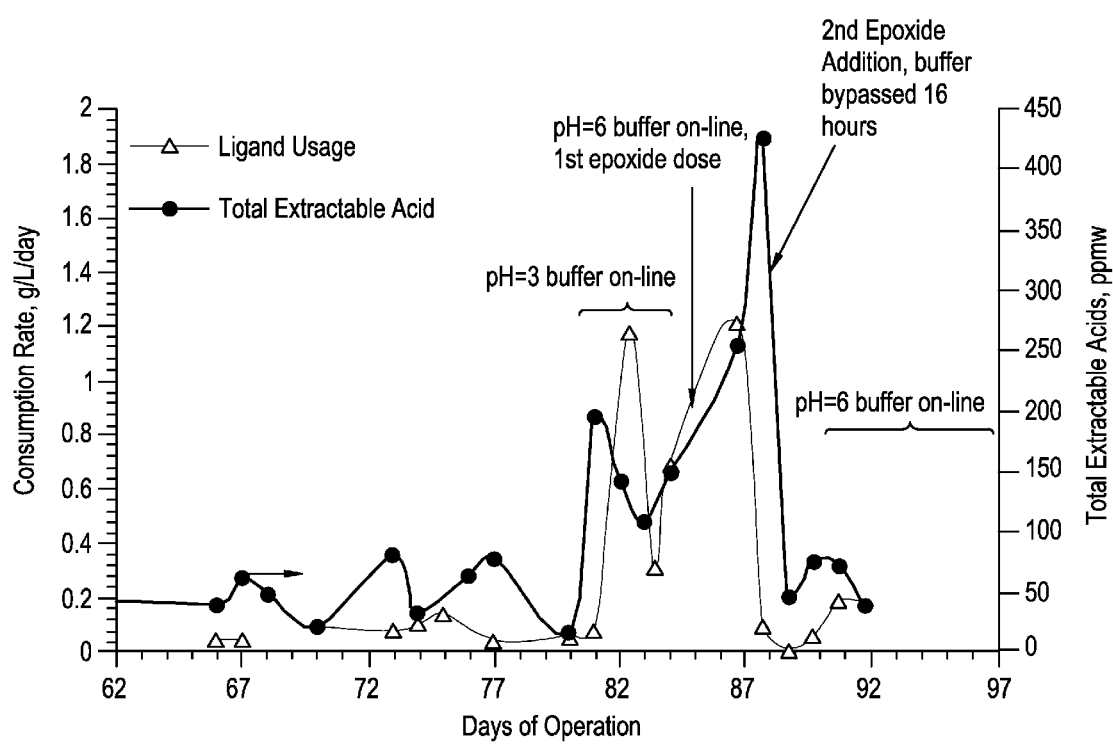

PROCESS FOR STABILIZING A PHOSPHITE LIGAND AGAINST DEGRADATION

CROSS-REFERENCE TO RELATED APPLICATIONS

This application claims priority from provisional application Ser. No. 61/705,194, filed Sep. 25, 2012, which is incorporated herein by reference in its entirety.

BACKGROUND OF THE INVENTION

The invention is directed to a process for increasing the stability of hydrolyzable organophosphorous ligands that are used in homogeneous catalysis.

Catalysts comprising a hydrolyzable organophosphorous ligand complexed with a transition metal, such as cobalt or rhodium, are used in many hydroformylation processes. The hydrolyzable organophosphorous ligand can be depleted via an autocatalytic reaction with other components of the hydroformylation reaction mixture.

U.S. Pat. Nos. 5,364,950 and 6,693,219 teach the use of an epoxide to remove acidic impurities in hydroformylation catalyst mixtures to prevent the buildup of acidic materials that cause the autocatalytic decomposition of hydrolyzable phosphorous ligands. U.S. Pat. Nos. 5,741,944 and 5,731,473 teach the use of an aqueous buffer extraction process to remove acids from a hydroformylation catalyst mixture. U.S. Pat. No. 5,767,321 discloses removing acidic impurities by either buffer washing or epoxide addition.

However, the prior art processes do not adequately deal with situations in which high amounts of acid are present, e.g., situations where process variations exist as a result of a process "upset" as in, for example, the case of a temporary extractor failure, the case of a problem with the buffer formulation, or the case of inadvertent addition of acid, etc.

High acid concentrations lead to the loss of highly expensive catalytic metal, which is detrimental to the economics of any commercial process. It would be desirable to have a process for mitigating the presence of acid impurities that (1) treats and removes the acid impurities in the entire reaction system, e.g., in the reactor and in peripheral equipment, and (2) is capable of rapid response to sudden acid increases.

SUMMARY OF THE INVENTION

The invention is such a process for stabilizing a phosphite ligand against degradation in a hydroformylation reaction fluid comprising a metal-organophosphite ligand complex catalyst and the phosphite ligand, said process comprising adding to the reaction fluid from 0.001 to 5 weight percent, based on the weight of the reaction fluid, of an epoxide, and further comprising separating one or more phosphorus acidic compounds from the reaction fluid by treating at least a portion of the reaction fluid with an aqueous buffer solution under conditions sufficient to neutralize and remove at least some amount of the phosphorus acidic compounds from the reaction fluid.

While it is known that epoxide treatment and buffer extraction can be used individually, we have found that epoxide addition used by itself unexpectedly loses efficacy over time, i.e., subsequent epoxide additions have diminishing benefits. Surprisingly, the process of the invention is capable of rapid response to sudden acid increases and has long-term efficacy.

BRIEF DESCRIPTION OF THE DRAWINGS

FIG. 1 is a graph of ligand usage and total extractable acid level vs. time for Example 1.

DETAILED DESCRIPTION OF THE INVENTION

The invention includes a process wherein aqueous buffer extraction is used to remove acidic impurities from a reaction fluid containing a hydrolyzable organophosphorous ligand, and wherein an epoxide is added to the reaction fluid. The reaction fluid may comprise CO, $H_2$, at least one olefin, and/or at least one aldehyde product in the presence of a catalyst comprising, as components, a transition metal and a hydrolyzable phosphorous ligand. Optional process components include an amine and/or water. The process increases the stability of the ligand against such degradation above that which the aqueous buffer extraction alone can provide.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and non-aromatic organic compounds, which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and non-aromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Hydrolyzable phosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites and fluorophosphites. The ligands may include chelate structures and/or may contain multiple P—Z moieties such as polyphosphites, polyphosphoramidites, etc. and mixed P—Z moieties such as phosphite-phosphoramidites and flurophosphite-phosphites.

The term "free ligand" means ligand that is not complexed with (tied to or bound to) the metal, e.g., metal atom, of the complex catalyst.

Hydrogen and carbon monoxide are required for hydroformylation. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons; and (2) the gasification of coal and/or biomass. Hydrogen and CO typically are the main components of syngas, but syngas may contain carbon dioxide and inert gases such as $N_2$ and Ar. The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications.

The substituted or unsubstituted olefinic unsaturated starting material reactants that may be employed in the hydroformylation process include both optically active (prochiral and chiral) and non-optically active (achiral) olefinic unsaturated compounds containing from 2 to 40, preferably 3 to 20, carbon atoms. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene, as disclosed, for example, in U.S. Pat. Nos. 4,518,809 and 4,528,403). Moreover, such olefin compounds may further contain one or more additional ethylenic unsaturated groups, and mixtures of two or more different olefinic unsaturated compounds may be employed as the starting hydroformylation material if desired. For example, commercial alpha olefins containing four or more carbon atoms may contain minor amounts of corresponding internal olefins and/or their corresponding saturated hydrocarbon and that such commercial olefins need not necessarily be purified from same prior to being hydroformylated. Illustrative mixtures of olefinic starting materials that can be employed in the hydroformylation reactions include, for example, mixed butenes, e.g., Raffinate I and II. Further such olefinic unsaturated compounds and the corresponding aldehyde products derived therefrom may also contain one or more groups or substituents that do not unduly adversely affect the hydroformylation process or the process of this invention such as described, for example, in U.S. Pat. Nos. 3,527,809 and 4,769,498.

Most preferably, hydroformylation is especially useful for the production of non-optically active aldehydes, by hydroformylating achiral alpha-olefins containing from 2 to 30, preferably 3 to 20, carbon atoms, and achiral internal olefins containing from 4 to 20 carbon atoms as well as starting material mixtures of such alpha olefins and internal olefins.

Illustrative alpha and internal olefins include, for example, ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, 2-octene, cyclohexene, propylene dimers, propylene trimers, propylene tetramers, butadiene, piperylene, isoprene, 2-ethyl-1-hexene, styrene, 4-methyl styrene, 4-isopropyl styrene, 4-tert-butyl styrene, alpha-methyl styrene, 4-tert-butyl-alpha-methyl styrene, 1,3-diisopropenylbenzene, 3-phenyl-1-propene, 1,4-hexadiene, 1,7-octadiene, and 3-cyclohexyl-1-butene, as well as, 1,3-dienes, butadiene, alkyl alkenoates, e.g., methyl pentenoate, alkenyl alkanoates, alkenyl alkyl ethers, alkenols, e.g., pentenols, alkenals, e.g., pentenals and other compounds, such as allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, allyl ethyl ether, n-propyl-7-octenoate, 3-butenenitrile, 5-hexenamide, eugenol, iso-eugenol, safrole, iso-safrole, anethol, 4-allylanisole, indene, limonene, beta-pinene, dicyclopentadiene, cyclooctadiene, camphene, and linalool.

Prochiral and chiral olefins useful in the asymmetric hydroformylation that can be employed to produce enantiomeric aldehyde mixtures include those represented by the formula:

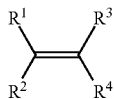

wherein $R^1$, $R^2$, $R^3$ and $R^4$ are the same or different (provided $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene.

Illustrative optically active or prochiral olefinic compounds useful in asymmetric hydroformylation include, for example, p-isobutylstyrene, 2-vinyl-6-methoxy-2-naphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene and phenyl vinyl ether. Other olefinic compounds include substituted aryl ethylenes as described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and methods for their preparation are well known in the art.

Representative monoorganophosphites may include those having the formula:

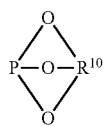

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals such as those derived from 1,3,5-trihydroxycyclohexane. Such monoorganophosphites may be found described in greater detail, for example, in U.S. Pat. No. 4,567,306.

Representative diorganophosphites may include those having the formula:

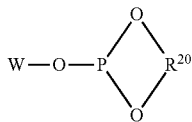

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene. More preferably $R^{20}$ is a divalent aromatic radical such as disclosed more fully, for example, in U.S. Pat. Nos. 4,599,206, 4,717,775, 4,835,299.

Representative of a more preferred class of diorganophosphites are those of the formula:

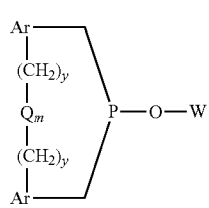

<<III>> wherein W is as defined above, each Ar is the same or different and represents a substituted or unsubstituted aryl radical, each y is the same or different and is a value of 0 or 1, Q represents a divalent bridging group selected from $—C(R^{33})_2—$, $—O—$, $—S—$, $—NR^{24}—$, $Si(R^{35})_2$ and $—CO—$, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, and triaryl phosphites, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl) cyclohexylphosphite, tris(3,6-di-t-butyl-2-naphthyl)phosphite, bis(3,6,8-tri-t-butyl-2-naphthyl)phenylphosphite, and bis(3,6,8-tri-t-butyl-2-naphthyl)(4-sulfonylphenyl)phosphite. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

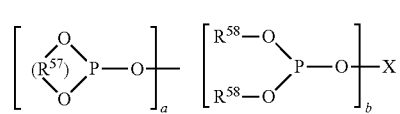

<<V>> wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and 5,527, 950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

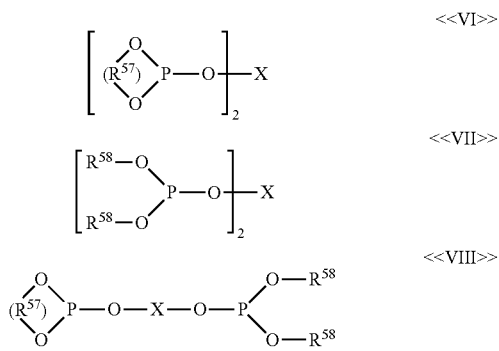

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^{35})_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired hydroformylation result. Substituents that may be on said radicals in addition to corresponding hydrocarbon radicals such as alkyl, aryl, aralkyl, alkaryl and cyclohexyl substituents, may include for example silyl radicals such as —$Si(R^{35})_3$; amino radicals such as —$N(R^{15})_2$; phosphine radicals such as -aryl-$P(R^{15})_2$; acyl radicals such as —$C(O)R^{15}$ acyloxy radicals such as —$OC(O)R^{15}$; amido radicals such as —$CON(R^{15})_2$ and —$N(R^{15})COR^{15}$; sulfonyl radicals such as —$SO_2R^{15}$, alkoxy radicals such as —$OR^{15}$; sulfinyl radicals such as —$SOR^{15}$, phosphonyl radicals such as —$P(O)(R^{15})_2$, as well as halo, nitro, cyano, trifluoromethyl, and hydroxy radicals, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{15})_2$ each $R^{15}$ taken together can also represent a divalent bridging group that forms a heterocyclic radical with the nitrogen atom, and in amido substituents such as —$C(O)N(R^{15})_2$ and —$N(R^{15})COR^{15}$ each $R^{15}$ bonded to N can also be hydrogen. It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and octadecyl; aryl radicals such as phenyl and naphthyl; aralkyl radicals such as benzyl, phenylethyl and triphenylmethyl; alkaryl radicals such as tolyl and xylyl; alicyclic radicals such as cyclopentyl, cyclohexyl, 1-methylcyclohexyl, cyclooctyl, and cyclohexylethyl; alkoxy radicals such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals such as phenoxy; as well as silyl radicals such as —$Si(CH_3)_3$, —$Si(OCH_3)_3$, and —$Si(C_3H_7)_3$; amino radicals such as —$NH_2$, —$N(CH_3)_2$, —$NHCH_3$, and —$NH(C_2H_5)$; arylphosphine radicals such as —$P(C_6H_5)_2$; acyl radicals such as —$C(O)CH_3$, —$C(O)C_2H_5$, and —$C(O)C_6H_5$; carbonyloxy radicals such as —$C(O)OCH_3$; oxycarbonyl radicals such as —$O(CO)C_6H_5$; amido radicals such as —$CONH_2$, —$CON(CH_3)_2$, and —$NHC(O)CH_3$; sulfonyl radicals such as —$S(O)_2C_2H_5$; sulfinyl radicals such as —$S(O)CH_3$; sulfonyl radicals such as —$SCH_3$, —$C_2H_5$, and —$SC_6H_5$; and phosphonyl radicals such as —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, and —$P(O)(H)(C_6H_5)$.

Specific illustrative examples of such organophosphite ligands include the following: 2-t-butyl-4-methoxyphenyl(3, 3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diy 1]bis(oxy)]bis-dibenzo [d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3', 5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldi phosphite, 2-[[2-[[4, 8,-bis(1,1-dimethylethyl), 2,10-dimethoxydibenzo-[d,f][1,3, 2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, and $Rh(NO_3)_3$ may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g., to maintain a predetermined level of free ligand in the reaction medium.

In one embodiment, the rhodium catalyst may be impregnated onto any solid support, such as inorganic oxides, (i.e., alumina, silica, titania, or zirconia) carbon, or ion exchange resins, supported on, or intercalated inside the pores of, a zeolite, glass or clay, or may also be dissolved in a liquid film coating the pores of said zeolite or glass. Such zeolite-supported catalysts are particularly advantageous for producing one or more regioisomeric aldehydes in high selectivity, as determined by the pore size of the zeolite. The solid catalyst thus formed may still be complexed with one or more of the ligands defined above. Descriptions of such solid catalysts may be found in for example: *J. Mol. Cat.* 1991, 70, 363-368; *Catal. Lett.* 1991, 8, 209-214; *J. Organomet. Chem,* 1991, 403, 221-227; *Nature,* 1989, 339, 454-455; *J. Catal.* 1985, 96, 563-573; *J. Mol. Cat.* 1987, 39, 243-259. The catalyst may be attached to a thin film or membrane support, such as cellulose acetate or polyphenylenesulfone, as described in, for example, *J. Mol. Cat.,* 1990, 63, 213-221. The catalyst may be attached to an insoluble polymeric support through an organophosphorus-containing ligand, such as a phosphite, incorporated into the polymer. Descriptions of polymer-supported catalysts may be found in for example: *J. Mol. Cat.,* 1993, 83, 17-35; *Chemtech* 1983, 46; *J. Am. Chem. Soc.,* 1987, 109, 7122-7127. In another embodiment, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer,* 1992, 33, 161; *J. Org. Chem.* 1989, 54, 2726-2730.

The use of an aqueous buffer solution to prevent and/or lessen hydrolytic degradation of an organophosphite ligand and deactivation of a metal-organophosphite ligand complex is disclosed in U.S. Pat. No. 5,741,942. Aqueous buffers used in U.S. Pat. No. 5,741,944 are generally salts of weak acids or bases but are usually Group 1 or 2 metal (Na, K, Ca, etc.) salts of weak acids. In some cases where amines are used, they generate ionic salts, such as ammonium salts, when they neutralize and remove at least some amount of the phosphorus acidic compounds from the reaction fluid. The aqueous buffer solutions employable in this invention may comprise any suitable buffer mixture containing salts of oxyacids, the nature and proportions of which in the mixture are such that the pH of their aqueous solutions may range from 3 to 9, preferably from 4 to 8 and more preferably from 4.5 to 7.5. In this context suitable buffer systems may include mixtures of anions selected from the group consisting of phosphate, carbonate, citrate, maleate, fumarate, and borate compounds and cations selected from the group consisting of ammonium and alkali metals, e.g., sodium, potassium and the like. Such buffer systems and/or methods for their preparation are well known in the art.

Illustrative metal-organophosphorous ligand complex catalyzed hydroformylation processes that may experience hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. P—Z containing species that will likely undergo hydrolytic degradation include organophosphonites, phosphoramidites and fluorophosphonites, such as described in WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be extracted by use of the extractor technology taught in U.S. Pat. Nos. 5,744,649 and 5,741,944. Accordingly, the hydroformylation processing techniques that are advantageously employed with the invention disclosed herein may correspond to any known processing techniques. Preferred hydroformylation processes are those involving catalyst liquid recycle.

The invention includes an extraction process for removing acidic impurities from the catalyst solution. Advantageously, the treated catalyst-containing fluid may be returned to a reaction zone of a hydroformylation process. The extraction process advantageously employs an aqueous buffer solution containing a metal salt of an oxyacid. The pH of this aqueous solution advantageously is in the range of 6-8 and the solution is capable of substantial buffering capacity within this range. The catalyst solution advantageously comprises an organophosphorous ligand and a metal-organophosphorous ligand complex, and the extraction process comprises the step of contacting the catalyst solution with an aqueous buffer solution within an extraction zone. In a continuous process, the extraction zone advantageously is located after the reaction zone. In one embodiment of the invention, a vaporizer follows the reaction zone to vaporize volatile components of the liquid effluent stream of the reaction zone. Any non-vaporized liquid is sent to the extraction zone. The aqueous buffer solution advantageously is used to accomplish at least one of the following: (1) stabilize the organophosphorous ligand against hydrolytic degradation, (2) stabilize the metal-organophosphorous ligand complex against degradation or deactivation, (3) reduce the concentration of ligand degradation products from the catalyst solution and (4) remove at least some of the epoxide-acid adducts.

Preferred buffer systems are phosphate buffers and time of contact with the reaction fluid, need only be that which is sufficient to neutralize at least some amount of the phosphorus acidic compounds that cause hydrolytic degradation of the desirable organophosphorous ligands. Preferably the amount of aqueous buffer solution is sufficient to at least maintain the concentration of such acidic compounds below the threshold level that causes substantial degradation of the hydrolyzable organophosphorous ligand. For instance, a preferred quantity of aqueous buffer solution is a quantity that ensures that any degradation of the organophosphorous ligand proceeds by the "non-catalytic mechanism" as described in "The Kinetic Rate Law for Autocatalytic Reactions" by Mata-Perez et al., *Journal of Chemical Education, Vol.* 64, No. 11, November 1987, pages 925 to 927, rather than by the "catalytic mechanism" described in said article. The amount of buffer correlates with buffer capacity or the amount of acid species that can be removed without significant change in the extraction fluid pH. The concentration of the unsaturated organic acid salt buffer is not narrowly critical. Advantageously, the concentration of the buffer salt in the buffer solution is from 0.001M to 0.8M and more preferably is from 0.01 to 0.04M. In one embodiment of the invention, the maximum aqueous buffer solution concentration is governed by practical considerations. The preparation of buffers is well known in the art. Advantageously, degassed ($O_2$-free) de-ionized water is employed in the preparation of the buffer solution. Mixtures of buffers may be employed.

The manner in which the metal-organophosphorous ligand complex catalyst containing reaction fluid and aqueous buffer solution are contacted, as well as the amount of aqueous buffer solution, temperature, pressure and contact time are not narrowly critical and need only be sufficient to obtain the results desired. For instance, said treatment may be carried out in any suitable vessel or container, e.g., any vessel suitable for use as a liquid/liquid extractor, that provides a suitable means for thorough contact between the reaction fluid and the aqueous buffer solution. In general, it is preferred to pass the reaction fluid through the aqueous buffer solution in a sieve tray extractor column in a countercurrent fashion.

Contacting conditions may vary greatly and any suitable combination of such conditions may be employed herein. For instance, a decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid according to the invention may be determined by measuring the rate of degradation (consumption) of the organophosphorous ligand present in the hydroformylation reaction medium. The consumption rate can vary over a wide range, e.g., from less than 0.06 up to 5 grams of ligand per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., less than 0.5 grams of ligand per liter per day, and more preferably less than 0.1 grams of ligand per liter per day, and most preferably less than 0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid and hydroxyl pentyl phosphonic acid, from the hydroformylation system allows one to control the acidity of the hydroformylation reaction medium, thereby stabilizing the useful organophosphorous ligand by preventing or lessening its hydrolytic decomposition. The need to control the acidity in organophosphorous promoted metal catalyzed hydroformylation is explained herein. Thus, the purpose of the buffer is to remove or reduce excessive acidity from the catalyst system in order to maintain a proper acidity level in the reaction fluid so that the consumption of the useful organophosphorous ligands do not hydrolytically degrade at an unacceptable rate while keeping catalyst activity at a productive level.

Optionally, an organic nitrogen compound may be added to the hydroformylation reaction fluid to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the catalytic metal from complexing with the acidic hydrolysis by-products and thus helping to protect the activity of the catalyst while it is present in the reaction zone under reaction conditions.

Preferred organic nitrogen compounds useful for scavenging the phosphorus acidic compounds are heterocyclic compounds selected from the group consisting of diazoles, triazoles, diazines and triazines, such as those disclosed in U.S. Pat. No. 5,731,472. Benzimidazole and benztriazole are preferred. The amount of organic nitrogen compound that may be present in the reaction fluid is typically sufficient to provide a concentration of at least 0.0001 moles of free organic nitrogen compound per liter of reaction fluid. In general, the ratio of organic nitrogen compound to total organophosphorous ligand (whether bound or present as free organophosphorous ligand) is at least 0.1:1 and even more preferably at least 0.5:1. Organic nitrogen compound: organophosphorous ligand molar ratios of from 1:1 to 5:1 should be sufficient for most purposes.

The aqueous buffer solution treatment will not only remove free phosphoric acidic compounds from the metal-organophosphorous ligand complex catalyst containing reaction fluids, but it also removes the phosphorus acidic material of the conversion product salt formed by the use of the organic nitrogen compound scavenger when employed, i.e., the phosphorus acid of said conversion product salt remains behind in the aqueous buffer solution, while the treated reaction fluid, along with the reactivated (free) organic nitrogen compound is returned to the reaction zone.

Moreover, removal of the desired aldehyde product can cause concentrations of the other ingredients of the reaction fluid to be increased proportionately. Thus, for example, the organophosphorous ligand concentration in the metal-organophosphorous ligand complex catalyst containing reaction fluid to be treated by the aqueous buffer in accordance with the process of this invention may range from between 0.005 and 15 weight percent based on the total weight of the reaction fluid. Preferably the ligand concentration is between 0.01 and 10 weight percent, and more preferably is between 0.05 and 5 weight percent on that basis. Similarly, the concentration of the metal in the metal-organophosphorous ligand complex catalyst containing reaction fluid to be treated by the aqueous buffer in accordance with the process of this invention may be as high as 5000 ppmw based on the weight of the reaction fluid. Preferably the metal concentration is between 50 and 2500 ppmw based on the weight of the reaction fluid, and more preferably is between 70 and 2000 ppmw.

Epoxides suitably utilized in the process of the invention include the epoxides having the formulas set forth below. The first such formula is as follows:

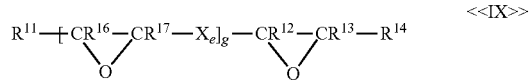 <<IX>> wherein:
(1) e is 0 or 1;
(2) g is 0 or 1;

(3) $R^{11}$, $R^{12}$, $R^{13}$, $R^{14}$, $R^{16}$ and $R^{17}$ are independently selected from the group consisting of hydrogen; monovalent hydrocarbon radicals (such as alkyl, aryl, aralkyl, and alkaryl groups having from 1 to about 30 carbon atoms; substituted alkyl, aryl, aralkyl and alkaryl groups having from 1 to about 30 carbon atoms; and groups wherein two or more of $R^{11}$, $R^{12}$, $R^{13}$, $R^{14}$, $R^{16}$ and $R^{17}$ are linked together to form a cyclic structure that has up to about 30 carbon atoms and may comprise a plurality of ring structures such as bicyclo-, tricyclo-, tetracyclo- and n-cyclo-groups;

(4) X is a divalent bridging group selected from the group consisting of substituted or unsubstituted alkylene, arylene, aralkylene, and alkarylene groups having up to about 30 carbon atoms, —O—, —S—NR$^{18}$—, —Si(R$^{19}$)$_2$—, and —CO— and wherein each radical $R^{18}$ and $R^{19}$ individually represents H or alkyl groups.

In this definition, the word "substituted" denotes presence of groups that do not react with epoxides, such as alkoxy and aryloxy groups. Excluded from the definition of "substituted" are halogens, alcohols, amines, carboxyl moieties, nitrile groups, and any other moieties that react with epoxides. Epoxides of the following formula generally are preferred.

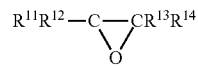 <<X>>

When e equals 0 and f equals 0 in formula (IX) above, epoxides suitable used in the process of this invention have the formula (X) wherein $R^{11}$, $R^{12}$, $R^{13}$, and $R^{14}$ are as described above with regard to formula (IX). Examples of suitable epoxides of formula (X) include, but are not limited to, 1,2-cyclohexene oxide; styrene oxide; propylene oxide; 1,2-octene oxide; 1,2-decene oxide; 1,2-dodecene oxide; 1,2-hexadecene oxide; 1,2-octadecene oxide; ethylene oxide; 1,2-cyclododecene oxide; stilbene oxide; isobutylene oxide; 2,3-epoxybutane; 1,2-epoxybutane; 1,2-epoxyhexane; cyclopentene oxide; cyclooctene oxide; cyclodecene oxide; and 1,2-epoxy-3-phenoxy-propane. Preferably $R^{11}$ and $R^{12}$ in formula (X) are hydrogen.

Epoxy compositions of formula (X) above having at least one ring in a cyclic structure formed by the combination of one of $R^{11}$ and $R^{12}$ groups with one of $R^{13}$ and $R^{14}$ groups include cyclic structures that have a plurality of rings associated therewith, including bicyclo- and other n-cyclo-groups. Bicyclo-groups are cyclic hydrocarbon groups consisting of two rings only having two or more atoms in common. Tricyclo-, tetracyclo-, and other n-cyclo-compounds also are included within the definition of cyclic structures having a plurality of rings. Examples of such plural ring structures within the scope of a cyclic structure formed by the combination of one of $R^{11}$ and $R^{12}$ groups with one of $R^{13}$ and $R^{14}$ groups include the bicyclo-compounds norbornane, which is also known as bicyclo[2.2.1]heptane, and α-pinene, which is also known as 2,7,7-trimethyl-Δ$_2$-bicyclo[1.1.3]heptene. Epoxy compounds that are formed from norbornane and α-pinene are 2,3-epoxynorbornane, which is also known as 2,3-epoxy-bicyclo[2.2.1]heptane), and α-pinene oxide.

Epoxy compounds useful in the process of this invention include those having a composition of formula (X) above, wherein the $R^{11}$ and $R^{12}$ groups together or the $R^{13}$ and $R^{14}$ groups together, or both, may form cyclic structure(s) that may include a plurality of rings. The cyclic structure of such compounds can include bicyclo-, tricyclo-, and other n-cyclo compounds. Nopinene, which is also known as β-pinene or 7,7-dimethyl-2-methylenenorpinane, is a composition having a ring structure that yields an epoxy compound useful in the invention. The epoxy compound derived from nopinene, β-pinene oxide, is a compound of formula (X) above wherein $R^{11}$ and $R^{12}$ form a cyclic structure having a plurality of ring structures, $R^{13}$ is a methyl group, and $R^{14}$ is hydrogen.

Diepoxides also are useful in the method of the invention. Suitable diepoxy compounds of formula (VI) include 1,3-butadiene diepoxide, 1,2,7,8-diepoxyoctane, diepoxycyclooctane, dicyclopentadiene dioxide, and 3,4-epoxy cyclohexyl methyl-3,4-epoxy cyclohexyl carboxylate (available as ERL-4221®, a trademark of Union Carbide Chemicals and Plastics Technology Corporation).

Supported epoxides such as those described in US 2012/0172630 are suitable as well.

The quantity of epoxide utilized in accordance with the process of this invention is that quantity sufficient to interact with the phosphorous acids that cause degradation of phosphite ligand-containing catalysts. Preferably, the quantity of epoxide is sufficient to maintain the concentration of acidic by-products below the threshold level that causes rapid degradation of the ligand. This preferred quantity of epoxide is the quantity that ensures that any degradation of the ligand proceeds by the "non-catalytic mechanism" as described in "The Kinetic Rate Law for Autocatalytic Reactions" by Mata-Perez et al, Journal of Chemical Education, Vol. 64, No. 11 Nov. 1987, pages 925 to 927 rather than by the "catalytic mechanism" described in that article. Most preferably, the quantity is sufficient to maintain the concentration of acidic catalysts at an essentially undetectable level.

A suitable concentration of epoxide in a hydroformylation reaction mixture used in the invention advantageously is at least 0.001 weight percent (per epoxide moiety) of the total weight of the reaction mixture. Typically, the maximum epoxide concentration is limited by practical considerations, such as the cost of epoxide and by the undesirable side effects of too much epoxide (e.g., the formation of acetal and polyether by-products and the possible contamination of the desired product with excess epoxide). Although the maximum epoxide concentration is not narrowly limited for the purpose of this invention, a maximum epoxide concentration in practice typically does not exceed about 5 weight percent of the total weight of the reaction mixture. The concentration of epoxide preferably at least about equals, and more preferably somewhat exceeds, a stoichiometric concentration required for the epoxide to interact with each phosphorous acid molecule produced during phosphite degradation. Typically, one epoxide group is required to interact with each phosphorous acid molecule. An excess of epoxide typically is not harmful and a stoichiometric deficiency of epoxide merely limits the effectiveness of the invention. Preferably, the epoxide concentration is maintained between about 0.01 and 2 weight percent based on the total weight of reaction mixture. Most preferably, the epoxide concentration is maintained between about 0.1 and 1 weight percent based on total weight of reaction mixture.

In the process of the present invention, the epoxide is added to and thoroughly mixed into the reaction mixture using any convenient procedure. The epoxide can be mixed with or dissolved in any of the reactant streams or solvent make-up streams or the epoxide periodically can be separately added to the reactant mixture. The epoxide can be added reaction mixture in small quantity over an extended period of operation. In this way, a concentration of epoxide effective to stabilize ligand during steady-state operation is obtained, with epoxide consumed by reaction with phosphorous acid as it is formed. The epoxide also can be added intermittently at a higher concentration, with the intent of achieving a long-term stabilization effect by starting at a higher-than-necessary concentration and allowing the concentration to fall to a more typical concentration during a period without injection addition. Alternatively, the epoxide is added only when needed to mitigate a higher-than-usual level of acid then discontinued when the acid level has dropped to the level the aqueous buffer extractor can remove at or greater than the rate of formation.

Without wishing to be bound by any particular theory, it appears that, in the process of the invention, the epoxide reacts with the phosphorous acids resulting from phosphite degradation and that reaction lowers the concentration of phosphorous acids and correspondingly reduces the formation of additional autocatalytically-produced phosphorous acids. In particular, it appears that the epoxide reacts with the phosphorus acids in accordance with the sequence of reactions that can be illustrated in U.S. Pat. No. 5,364,950 (col. 10). The invention is believed to operate by converting such aldehyde acids to relatively inert adducts (e.g., Adduct 2 in the above referenced reaction sequence in U.S. Pat. No. 5,364,950). The resulting polar adducts are then removed by the extractor in the aqueous layer thus avoiding buildup of Adduct 2, which may be capable of reversing to regenerate the acid (or contribute to the level of undesirable heavies in the reaction system).

We have observed that continuous epoxide addition (without the presence of the extractor) loses effectiveness over prolonged times. One possible explanation is that the buildup of Adduct 2 materials may result in the reverse reaction becoming significant, thereby regenerating the acidic species.

Regardless of the specific mechanism involved in the ligand stabilization of the process of the invention, the use of epoxides in accordance with this invention advantageously reduces the acidity of the reaction mixtures employed. Thus, in order to reduce ligand usage, it is preferred to minimize the molar ratio of any acid to the transition metal in the reaction mixture. Advantageously, the average ratio of acid to transition metal over sustained periods of time is no greater than 50:1, preferably no greater than 5:1, more preferably no greater than 1:1 and most preferably no greater than 0.05:1.

The process of the invention advantageously can bring unusually high concentrations of acids down to levels that the aqueous buffer extraction system can remove at the rate of formation. Thus the epoxide addition need not remove all or even most of the acid present in the system, but need only reduce it sufficiently for the aqueous buffer system to remove. The aqueous buffer system has limitations, such as it can only remove acid within the extraction zone whereas the epoxide present in the reaction zone can neutralize the acids as soon as they are formed in the heated reaction zone, thus minimizing their contribution to further ligand decomposition.

It was observed that continuous epoxide addition (without the presence of the extractor) loses effectiveness over prolonged times. See Comparative Experiment A hereinbelow. Without wishing to be bound by any theory, one possible explanation is that the buildup of Adduct 2 materials may result in the reverse reaction becoming significant, regenerating the acidic species. Since epoxides are known to react with water and alcohols, it is surprising that the addition of epoxide would scavenge low concentrations of acids in the presence of many orders of magnitude higher concentrations of water and alcohols.

However, the extractor has limited capability to respond to sudden acid increases or other process upsets that the epoxide addition can rapidly correct if added promptly. The two techniques can be thought of as complementary but operate best when done sequentially (e.g., avoiding loss of epoxide out the extractor aqueous tails).

The hydroformylation process may be asymmetric or non-asymmetric, the preferred processes being non-asymmetric, and may be conducted in any continuous or semi-continuous fashion and may involve any catalyst liquid and/or gas recycle operation desired. Thus, it should be clear that the particular hydroformylation process for producing such aldehydes from an olefinic unsaturated compound, as well as the reaction conditions and hydroformylation reaction ingredients of the hydroformylation process are not critical features of this invention.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. No. 5,430,194 and U.S. Pat. No. 5,681,473, or by the more conventional and preferred method of distilling it, i.e., vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction fluid employable herein includes any fluid derived from any corresponding hydroformylation process that contains at least some amount of four different main ingredients or components, i.e., the aldehyde product, a metal-organophosphorous ligand complex catalyst, free organophosphorous ligand and an organic solubilizing agent for said catalyst and said free ligand, said ingredients corresponding to those employed and/or produced by the hydroformylation process from whence the hydroformylation reaction mixture starting material may be derived. It is to be understood that the hydroformylation reaction mixture compositions employable herein can and normally will contain minor amounts of additional ingredients such as those that have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process may include any suitable type hydroformylation conditions heretofore employed for producing optically active and/or non-optically active aldehydes. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, $H_2$:CO molar ratio of gaseous hydrogen to carbon monoxide may range from 1:10 to 100:1 or higher, the more preferred hydrogen to carbon monoxide molar ratio being from 1:10 to 10:1.

In general, the hydroformylation process may be conducted at any operable reaction temperature. Advantageously, the hydroformylation process is conducted at a reaction temperature from $-25°$ C. to $200°$ C. In general, hydroformylation reaction temperatures of $50°$ C. to $120°$ C. are preferred for all types of olefinic starting materials. It is to be understood that when non-optically active aldehyde products are desired, achiral type olefin starting materials and organophosphorous ligands are employed and when optically active aldehyde products are desired prochiral or chiral type olefin starting materials and organophosphorous ligands are employed. It is to be also understood that the hydroformylation reaction conditions employed will be governed by the type of aldehyde product desired.

The hydroformylation process may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low. The at least one reaction zone employed in this invention may be a single vessel or may comprise two or more discrete vessels. The at least one separation zone employed in this invention may be a single vessel or may comprise two or more discrete vessels. The at least one buffer treatment zone employed in this invention may be a single vessel or may comprise two or more discreet vessels. It should be understood that the reaction zone(s) and separation zone(s) employed herein may exist in the same vessel or in different vessels. For example, reactive separation techniques such as reactive distillation and reactive membrane separation may occur in the reaction zone(s).

The hydroformylation process can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be substantially inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes may be carried out in a multistaged reactor such as described, for example, in U.S. Pat. No. 5,728,893. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

It is generally preferred to carry out the hydroformylation processes in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation, which is described, for example in U.S. Pat. Nos. 5,430,194 and 5,681,473.

As indicated above, desired aldehydes may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g., $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g., vaporizer/separator, wherein the desired aldehyde product is distilled. In general, distillation pressures ranging from vacuum pressures on up to total gas pressure of 340 kPa should be sufficient for most purposes.

One aspect of the invention is using an epoxide additive to rapidly lower acid levels in a process where an aqueous extractor is the normal and primary means of acid mitigation. For instance, if the pH of the aqueous buffer in the extractor inadvertently falls below the desired range, a period of higher than normal ligand hydrolysis may occur. The resulting acidic by-products will further catalyze additional ligand hydrolysis if left unchecked. Because only a small part of the reaction fluid is contacted with the aqueous buffer at any given time, recovering from such a rapid hydrolysis incident may be slow and can negatively impact production. Adding the epoxide directly to the reaction fluid will allow the system to recover more rapidly and return to normal operation in a shorter period of time.

In a second aspect, the invention involves the complementary use of an epoxide additive in a process that employs an aqueous buffer extractor. This process is intended to lower the intrinsic hydrolysis rate of a hydroformylation process. For instance, during normal operation, hydrolyzable organophosphorous ligands will be consumed by the process at a rate that is determined by several key factors, one of which is the concentration of acidic by-products in the reaction fluid. Using the epoxide additive on a routine basis to lower the inherent concentration of acidic by-products in the reaction fluid to below levels achievable when using the aqueous buffer extractor alone will slow the intrinsic hydrolysis rate and thus reduce consumption of the organophosphorous ligand.

In a third aspect, the invention involves the use of epoxide as the primary means of controlling acid concentration, with the use of the buffer extraction process as needed.

The process can be operated in several modes. In one embodiment of the invention, the epoxide addition is performed on a continuous manner, while in another embodiment, the epoxide addition is done on an as-needed or intermittent basis. In one embodiment of the invention, the buffer extraction is performed on a continuous manner, while in another embodiment, the buffer extraction being performed on an as-needed or non-continuous basis, e.g., in batch mode. Any combination of these modes may be employed.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, adipaldehyde, 2-methylglutaraldehyde, 2-methyladipaldehyde, 3-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, undecanal, 2-methyl 1-decanal, dodecanal, 2-methyl 1-undecanal, tridecanal, 2-methyl 1-tridecanal, 2-ethyl, 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonodecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal and 2-methyl-1-triacontanal.

Illustrative optically active aldehyde products include (enantiomeric) aldehyde compounds prepared by the asymmetric hydroformylation process such as, e.g., S-2-(p-isobutylphenyl)-propionaldehyde, S-2-(6-methoxy-2-naphthyl) propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]propionaldehyde and S-2-(2-methylacetaldehyde)-5-benzoylthiophene.

SPECIFIC EMBODIMENTS OF THE INVENTION

All parts and percentages in the following examples are by weight unless otherwise indicated. Pressures are given as absolute pressure unless otherwise indicated.

General Procedure

Three 1-liter stainless steel stirred tank reactors are connected in series to form a liquid recycle reactor system. Each reactor is equipped with a vertically mounted agitator and a circular tubular sparger located near the bottom of the reactor. Each sparger contains a plurality of holes of sufficient size to provide the desired gas flow into the liquid body in the reactor. The spargers are used for feeding the olefin and/or syngas to the reactor, and can also be used to recycle unreacted gases to each reactor. Each reactor has a silicone oil shell as a means of controlling reactor temperature. Reactors 1 to 2 and reactors 2 to 3 are further connected via lines to transfer any unreacted gases and lines to allow a portion of the liquid solution containing aldehyde product and catalyst to be pumped from reactor 1 to reactor 2 and from reactor 2 to reactor 3. Hence, the unreacted olefin of reactor 1 is further hydroformylated in reactor 2 and subsequently reactor 3. Each reactor also contains a pneumatic liquid level controller for maintaining the desired liquid level. Reactor 3 has a blow-off vent for removal of unreacted gases.

A portion of the liquid reaction solution is continuously pumped from Reactor 3 to a vaporizer, which consists of a heated vessel at reduced pressure. The effluent stream from the vaporizer is sent to a gas-liquid separator located at the bottom of the vaporizer, where vaporized aldehyde is separated from the non-volatile components of the liquid reaction solution. The vaporized aldehyde product is condensed and collected in a product receiver. A pneumatic liquid level controller controls the desired non-volatile component level, including catalyst to be recycled, at the bottom of the separator. The separator is connected to the buffer treatment vessel by a recycle line.

The non-volatile components, including catalyst to be recycled, from the separator are passed into the bottom of an aqueous buffer treatment zone, or extractor, which consists of a phase separation zone and a packed column contacting region. Following the buffer treatment, the organic layer, which contains catalyst to be recycled, is pumped from the phase separation zone through a recycle line into Reactor 1. The buffer (aqueous) layer is replaced on a periodic basis when the pH drops below 6.5 (or when the pH drops by 0.3 pH unit from the initial pH (e.g., 6.8).

The rate of ligand decomposition is monitored by removing samples from the recycle stream and analyzing by HPLC. Acid levels are determined by taking additional samples from the recycle stream. The organic samples are contacted with water to extract the hydroxyl alkyl phosphonic and phosphorous acids and the resulting aqueous phase is analyzed by Ion Chromatography (IC).

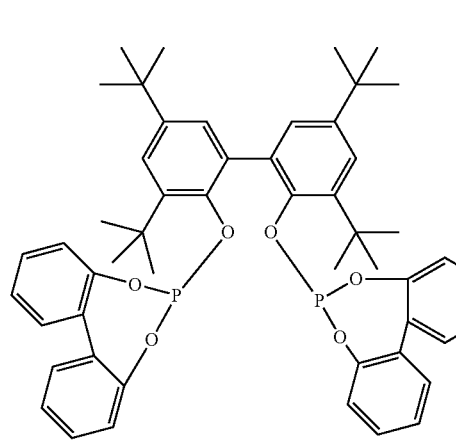

Ligand A

Example 1

The General Procedure described hereinabove is employed. A catalyst solution of rhodium (90 ppm) and Ligand A is employed for the hydroformylation of 1-butene at 110 psig of 1:1 $CO:H_2$. The molar ratio of Ligand A to rhodium is initially 2, and is maintained at about 2 during the reaction. Ligand usage and total extractable acid level are plotted vs. time in FIG. 1. After a long period of stable operation, a period of high ligand usage is triggered by changing the buffer pH to pH=3 for 3 days. The ligand usage and measured acid (as $H_3PO_3$ and hydroxypentylphosphonic acid, measured by IC) concentration rapidly increase (region A) and remain variable and high through region B. The extractor is bypassed for approximately 30 minutes, a time sufficient to replace the pH=3 buffer with fresh pH=6 buffer. During this time, a first addition of 5,000 ppm 1,2-epoxydodecane is introduced into the recycle line before the extractor. Circulation of the recycle catalyst stream through the extractor is then restored, using the moderate pH=6 buffer. Ligand usage is not immediately reduced, but falls sharply by region C, 2.5 days of operation later. However, measured acid levels are still high and appear to be increasing rapidly.

A second injection of epoxide, at the 5,000 ppm level, is performed to remove more acid and to confirm the impact of the epoxide addition. In this case, the injection is performed with the extractor by-passed during the addition and overnight (~16 hours) then the extractor is turned back on. The second epoxide charge has a very dramatic effect on acid concentration (region D).

The second epoxide addition results in a very dramatic improvement in the epoxide behavior—a low ligand degradation rate is maintained and acid levels are reduced to the low previous levels. Further analysis reveals that the epoxide is present in the catalyst solution for days after each injection (including the first injection). It is surprising that epoxide is detected by GC analysis for 7 days after the first addition indicating the extractor is not removing it due to side reactions with water or alcohols.

Comparative Experiment A

A liquid recycle hydroformylation demonstration system is operated with only 2 reactors, and is otherwise identical to the equipment described above. In this run epoxide addition is used but the extractor is not used during the entire demonstration period. Epoxide (1,2-dodecylepoxide) is added as needed in an attempt to meet the objective of keeping the acid concentration (as measured by IC) below 100 ppm. During the course of the demonstration, the effectiveness of the epoxide to control acid levels diminishes.

Table 1 shows the concentration of acid species, as measured from the recycle stream, over a 114 day testing period using different epoxide addition schedules. During the first 20 days a concentration of 2,000 ppmw epoxide and a frequency of 1 week is employed. This appears to be effective, and subsequently a lower concentration, 1,000 ppmw, is added more frequently through day 47. By day 47 the addition strategy becomes less effective as acid levels rise above 100 ppmw and the epoxide additions appear to be less effective at reducing the acid concentration. From day 50 to day 70, epoxide is added at a higher concentration and more frequently as acid levels climb to several hundred ppmw.

Example 2

Continuing the run of Comparative Experiment A, at day 70 all of the reaction fluid is drained from the reactor system into a 4 liter glass jug under nitrogen and is gently mixed with 2400 ml of aqueous 0.8 M sodium phosphate buffer (pH=6.8) to form a biphasic mixture. The catalyst is subsequently returned to the unit for additional testing. It is observed that after the buffer contacting (wash), acid levels remain low for 10 days without epoxide addition. An additional 44 days of testing is performed using a 5,000 ppmw epoxide dose at a week or more frequency. This maintains low acid levels through day 114. The data shows that the use of a periodic extraction step renders the epoxide addition process more effective for prolonged production times. This is surprising in that the unknown mechanism that renders the epoxide addition less effective is negated by the buffer extraction, and subsequent epoxide additions are effective in maintaining low acid levels.

TABLE 1

Acid concentration during period epoxide addition

| Days online | Total Acid (ppmw) | Days since last dosage | Epoxide dosage after acid samples (ppmw) |
|---|---|---|---|
| 3 | 23.0 | 0 | 2000 |
| 8 | 45.1 | | |
| 10 | 72.6 | 7 | 2000 |
| 15 | 68.6 | | |
| 17 | 81.8 | 7 | 2000 |
| 21 | 17.8 | | |
| 23 | 72.2 | 6 | 1000 |
| 27 | 139.1 | | |
| 28 | 88.4 | | |
| 29 | | 6 | 1000 |
| 33 | | 4 | 1000 |
| 34 | 28.5 | | |
| 36 | 76.2 | 3 | 1000 |
| 40 | | | 1000 |
| 41 | 131.2 | | |
| 43 | 174.7 | 3 | 1000 |
| 45 | 155.0 | | |
| 47 | | 4 | 1000 |
| 48 | 257.2 | | |
| 50 | 286.0 | 3 | 2000 |
| 52 | 362.2 | | |
| 55 | 304.2 | 5 | 5000 |
| 56 | 318.1 | | |
| 57 | 438.8 | 2 | 5000 |
| 58 | 386.7 | | |
| 59 | 185.7 | | |
| 61 | | 4 | 5000 |
| 62 | 475.7 | | |
| 63 | 137.5 | 2 | 5000 |
| 64 | 88.1 | | |
| 65 | 56.4 | | |
| 66 | 128.9 | | |
| 69 | 102.4 | | |
| 70 | Offline Catalyst Wash with Buffer | | |
| 77 | 19.2 | | |
| 78 | 27.4 | | |
| 79 | 21.4 | | |
| 80 | 23.9 | 0 | 5000 |
| 83 | 28.3 | | |
| 84 | 11.6 | | |
| 85 | 14.9 | | |
| 86 | 10.5 | | |
| 87 | 15.8 | 7 | 5000 |
| 90 | 142.7 | | |
| 92 | 27.4 | 5 | 5000 |
| 93 | 28.5 | | |
| 94 | 64.7 | | |
| 101 | | 9 | 5000 |
| 105 | 35.5 | | |
| 106 | 54.8 | | |
| 107 | 87.5 | 6 | 5000 |
| 112 | 53.5 | | |
| 114 | 72.7 | | |

What is claimed is:

1. A process for stabilizing a phosphite ligand against degradation in a hydroformylation reaction fluid comprising a metal-organophosphite ligand complex catalyst and the phosphite ligand, said process comprising adding to the reaction fluid from 0.001 to 5 weight percent, based on the weight of the reaction fluid, of an epoxide, and further comprising separating one or more phosphorus acidic compounds from the reaction fluid by treating at least a portion of the reaction fluid with an aqueous buffer solution under conditions sufficient to neutralize and remove at least some amount of the phosphorus acidic compounds from the reaction fluid.

2. The process of claim 1 wherein the epoxide addition is performed in a continuous manner.

3. The process of claim 1 wherein the epoxide addition is performed on an as-needed or intermittent basis.

4. The process of claim 1 wherein the buffer extraction is performed in a continuous manner.

5. The process of claim 1 wherein the buffer extraction being performed on an as-needed or intermittent basis.

6. The process of claim 5 wherein the buffer extraction is performed in a batch-mode.

7. The process of claim 1 wherein the reaction fluid further comprises an amine.

8. The process of claim 1 wherein the metal of the catalyst is Rh.

9. The process of claim 1 wherein at least a portion of the epoxide is added to a reactor.

10. The process of claim 1 wherein the reaction fluid comprises an organic phase and the aqueous buffer solution comprises a separate aqueous phase.

11. A process for stabilizing a phosphite ligand against degradation in a hydroformylation reaction fluid comprising a metal-organophosphite ligand complex catalyst and the phosphite ligand, said process comprising adding to the reaction fluid from 0.001 to 5 weight percent, based on the weight of the reaction fluid, of an epoxide, wherein at least a portion of the epoxide is added to a reactor, and then separating one or more phosphorus acidic compounds from the reaction fluid by treating at least a portion of the reaction fluid with an aqueous buffer solution in an extractor under conditions sufficient to neutralize and remove at least some amount of the phosphorus acidic compounds from the reaction fluid.

* * * * *